(12) United States Patent
Drake et al.

(10) Patent No.: US 8,042,273 B2
(45) Date of Patent: Oct. 25, 2011

(54) SLITTER WITH MECHANICAL HOLDING FINGER

(75) Inventors: Ron A. Drake, St. Louis Park, MN (US); Stanten C. Spear, Arden Hills, MN (US); Johnson E. Goode, Austin, TX (US); Beth C. Bullemer, Maple Plain, MN (US); Les Stener, Blaine, MN (US); Gary R. Fiedler, Forest Lake, MN (US); Kendra Yasger, Big Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 148 days.

(21) Appl. No.: 11/844,932

(22) Filed: Aug. 24, 2007

(65) Prior Publication Data

US 2009/0054840 A1    Feb. 26, 2009

(51) Int. Cl.
*B21F 13/00*    (2006.01)
*B26B 27/00*    (2006.01)
*A61M 5/178*    (2006.01)

(52) U.S. Cl. .................................. 30/90.4; 604/164.05
(58) Field of Classification Search ................. 604/160, 604/161, 164.05; 30/90.1, 90.4, 90.8, 91.1, 30/91.2, 92.5, 280, 286, 289, 290, 291, 293, 30/294
See application file for complete search history.

(56) References Cited

U.S. PATENT DOCUMENTS

| | | |
|---|---|---|
| 2,018,149 A | 10/1935 | Randle et al. |
| 3,057,232 A * | 10/1962 | Cornell, Jr. ................ 30/90.1 |
| 3,624,901 A | 12/1971 | Pettit et al. |
| 3,793,682 A | 2/1974 | Nelson |
| 3,898,733 A | 8/1975 | Cormier |
| 4,394,828 A | 7/1983 | Garbis et al. |
| 4,631,059 A | 12/1986 | Wolvek et al. |
| 4,687,469 A | 8/1987 | Osypka |
| 4,997,424 A | 3/1991 | Little |
| 5,188,606 A | 2/1993 | Maloney et al. |
| 5,261,887 A | 11/1993 | Walker |
| 5,330,460 A | 7/1994 | Moss |
| 5,359,690 A | 10/1994 | Kaizu et al. |
| 5,687,727 A | 11/1997 | Kraus et al. |
| 5,873,858 A | 2/1999 | Schafer et al. |
| D433,929 S | 11/2000 | Petzel |
| 6,148,521 A | 11/2000 | Eslambolchi et al. |
| 6,159,198 A | 12/2000 | Gardeski et al. |
| 6,247,235 B1 | 6/2001 | Lawler |
| 6,280,433 B1 | 8/2001 | McIvor et al. |

(Continued)

FOREIGN PATENT DOCUMENTS

WO    WO 01/02047 A1    1/2001

(Continued)

OTHER PUBLICATIONS

U.S. Appl. No. 12/182,659, filed Jul. 30, 2008, Duffy.

(Continued)

*Primary Examiner* — Nicholas D Lucchesi
*Assistant Examiner* — Nathan R Price
(74) *Attorney, Agent, or Firm* — Carol F. Barry (57) ABSTRACT

A slitter for slitting a guide catheter is assembled from a handle, a blade assembly coupled to the handle, and a holding mechanism coupled to the handle. The blade assembly includes a shroud for receiving an elongated body of a medical device and a slitting blade having an exposed cutting edge to slit the guide catheter.

50 Claims, 9 Drawing Sheets

U.S. PATENT DOCUMENTS

| | | | |
|---|---|---|---|
| 6,334,253 B1 * | 1/2002 | Cheng | 30/90.7 |
| 6,368,337 B1 | 4/2002 | Kieturakis et al. | |
| 6,497,681 B1 | 12/2002 | Brenner | |
| 6,544,247 B1 | 4/2003 | Gardeski et al. | |
| 7,029,460 B2 | 4/2006 | Gardeski et al. | |
| 7,338,481 B2 | 3/2008 | Gardeski et al. | |
| D576,279 S | 9/2008 | Bullemer et al. | |
| D576,280 S | 9/2008 | Bullemer et al. | |
| 7,462,167 B2 | 12/2008 | Kratz et al. | |
| 2003/0158565 A1 | 8/2003 | Gardeski et al. | |
| 2003/0181935 A1 | 9/2003 | Gardeski et al. | |
| 2005/0182435 A1 | 8/2005 | Andrews et al. | |
| 2007/0079511 A1 | 4/2007 | Osypka | |
| 2007/0175049 A1 | 8/2007 | Goode et al. | |
| 2008/0108972 A1 | 5/2008 | Andrews et al. | |
| 2009/0049698 A1 | 2/2009 | Drake et al. | |
| 2009/0071012 A1 | 3/2009 | Shan et al. | |
| 2010/0030154 A1 | 2/2010 | Duffy | |
| 2010/0030161 A1 | 2/2010 | Duffy | |
| 2011/0000089 A1 | 1/2011 | Goode et al. | |

FOREIGN PATENT DOCUMENTS

| | | |
|---|---|---|
| WO | 2006085119 A1 | 8/2006 |
| WO | WO 2007/089985 A1 | 8/2007 |
| WO | WO 2009/029558 A2 | 3/2009 |
| WO | WO 2009/029573 A1 | 3/2009 |
| WO | WO 2009/029558 A3 | 9/2009 |

OTHER PUBLICATIONS

U.S. Appl. No. 29/323,518, filed Aug. 27, 2008, Bullemer et al.
U.S. Appl. No. 29/323,574, filed Aug. 27, 2008, Bullemer et al.
PCT Search Report, PCT/US2008/074202, 2008.
6218RED Guide Catheter Slitter Technical Manual, Medtronic, Inc., Minneapolis, MN, Oct. 2002; 16 pgs.

* cited by examiner

SLITTER WITH MECHANICAL HOLDING FINGER

CROSS REFERENCE TO RELATED APPLICATION

Reference is made to the following commonly-assigned applications: Application Ser. No. 29/283,867 filed on even date herewith by Bullemer et al.; Application Ser. No. 29/283,864 filed on even date herewith by Bullemer et al.; and Application Ser. No. 11/844,912 filed on even date herewith by Drake et al., the entire contents of each disclosure are incorporated herein by reference.

TECHNICAL FIELD

The invention relates generally to implantable elongated medical device delivery systems and, in particular, to a slitter for slitting a guide catheter during removal from an implanted elongated medical device.

BACKGROUND

Elongated medical devices are often deployed to a targeted internal body location using a guide catheter or introducer. Examples of elongated medical devices include implantable medical electrical leads, such as cardiac pacing and sensing leads, and diagnostic or therapeutic catheters, such as electrophysiological mapping catheters and drug delivery catheters. The guide catheter is typically introduced into a blood vessel and the distal end of the guide catheter is advanced to a desired body site. The elongated medical device is then advanced through the guide catheter to the targeted site. While maintaining the elongated medical device in the desired position, the guide catheter is withdrawn over the elongated device body, leaving the device in position for monitoring physiological signals or delivering a therapy, such as an electrical stimulation therapy or a pharmacological or biological agent.

Depending on the targeted location and lead/catheter size, the guide catheter may be made with a relatively small diameter in order to allow advancement into narrow veins or arteries. The elongated medical device often includes a connector assembly or hub at a proximal end of the elongated body that is larger in diameter than the inner diameter of the guide catheter. As such, removal of the guide catheter often requires the use of a "slitter", which is used to slit the guide catheter open as it is withdrawn over the elongated medical device for removal. Because guide catheters and therapy delivery or diagnostic leads and catheters are available in a range of sizes, the slitter may be size specific so that it can be secured to the elongated device body and held in a stable position while the guide catheter is slit and removed. As such, a correctly-sized slitter may be required with a particular lead/catheter system.

Positioning a diagnostic or therapeutic lead/catheter at a desired location can be a time-consuming task requiring considerable skill. Once positioned, a physician must carefully remove the guide catheter without dislodging the lead/catheter from its desired location. If dislodgement occurs, repositioning is required which may involve reinserting the guide catheter. As such, a slitter needs to be easy to handle with one hand while the physician carefully withdraws the guide catheter with the other hand, all the time allowing the lead/catheter position to be stably maintained.

DETAILED DESCRIPTION

In the following description, references are made to illustrative embodiments for carrying out the invention. It is understood that other embodiments may be utilized without departing from the scope of the invention. For purposes of clarity, the same reference numbers are used in the drawings to identify similar elements. Unless otherwise indicated, drawing elements are not drawn to scale.

Figure 1A:
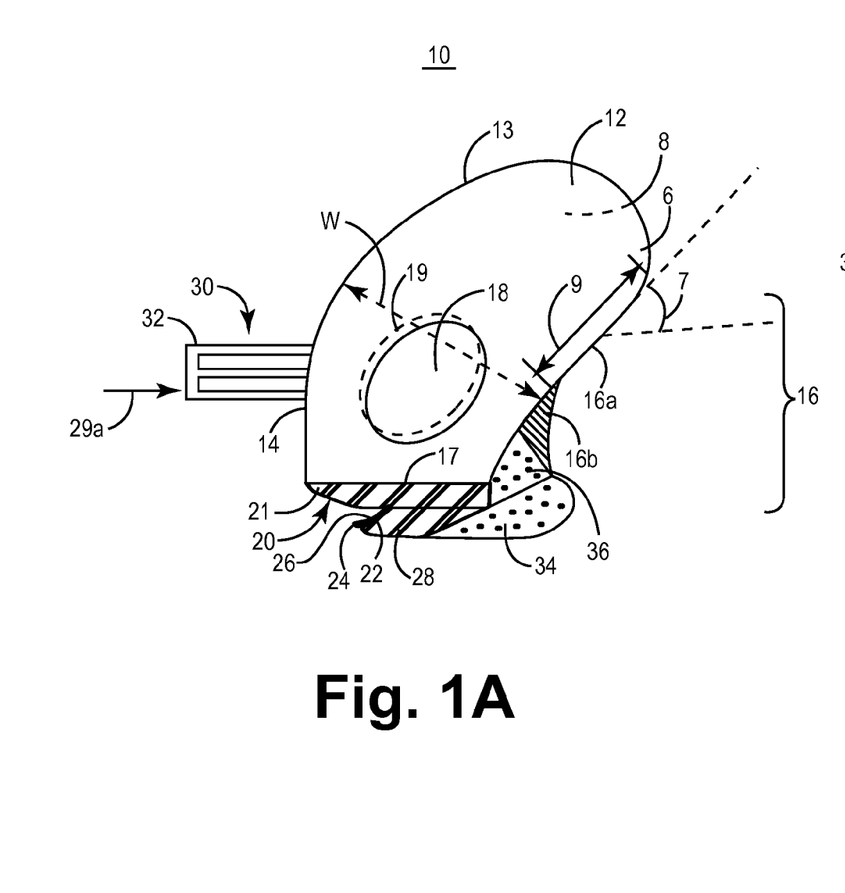
FIGS. 1A and 1B are plan views of a slitter used for removing a guide catheter from an implanted elongated medical device showing a holding mechanism in closed and open positions, respectively.
Figure 1B:
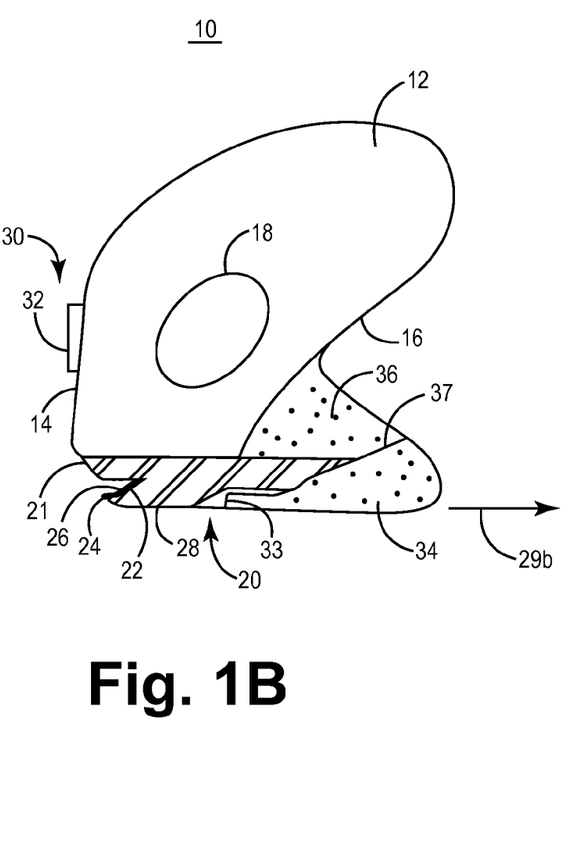

FIGS. 1A and 1B are plan views of a slitter for slitting a guide catheter during removal from an implanted elongated medical device. Slitter 10 includes a handle 12, a blade assembly 20 and a holding mechanism 30. The holding mechanism 30 stably secures the slitter 10 to the elongated body of a therapeutic or diagnostic medical lead or catheter being deployed to a target location through a guide catheter. As used herein, "guide catheter" refers to any elongated tubular device used in the implantation and delivery of an implantable elongated medical device, such as a medical electrical lead or diagnostic or fluid delivery catheter. As such, the term "guide catheter" as used herein collectively refers to devices also commonly referred to as "introducers" and "delivery catheters".

Handle 12 includes a forward edge 14 and a back edge 16 separating major sides 6 and 8. Handle 12 is generally shaped to enable a physician to comfortably and ergonomically grip slitter 10 using a substantially "whole-hand" grip. Handle 12 may include depressions 18 and 19 along major sides 6 and 8, respectively, or other features for promoting a secure grip and reducing slippage in the physician's hand. Other such features may include ridges, grooves, and roughened or slip-resistant surfaces.

In the particular embodiment shown, handle 12 includes an arcuate top edge 13 and horizontal bottom edge 17 extending between forward edge 14 and back edge 16 with depression 18 formed on major side 6 and an opposing depression 19 formed on opposite major side 8. Back edge 16 includes a generally straight, sloped portion 16a and an arcuate portion 16b. Sloped portion 16a slopes at an angle 7 relative to horizontal lower edge 17. Angle 7 is approximately 45 degrees in one embodiment and may range from, but is not limited to, 25 degrees to 75 degrees. Arcuate portion 16b is provided with a radius of approximately 0.25 inches in one embodiment but may be formed with a larger or smaller radius in various embodiments.

Handle 12 is thus configured to allow a physician to grip slitter 10 using one hand, either left or right, by placing a thumb over one depression 18 on major side 6 (for a right-handed user) and a forefinger over the opposite depression 19 on major side 8 and wrapping one, two or all three remaining fingers along the opposite major side 8 and around the sloped portion 16a of back edge 16. In this way, a physician may grasp handle 12 using a whole hand grip. As used herein, a "whole hand" grip refers to a grip or grasp that allows the handle to rest against the palm of the user's hand in contrast to a grip or grasp that results in contact with only the thumb and one or more finger tips. By pinching handle 12 between a forefinger and thumb placed over opposite depressions 18 and 19 and wrapping one or more fingers around back edge 16, handle 12 rests against the palm of the physician's hand. Alternatively, a forefinger may be positioned over actuator 32 for activating the slitter holding mechanism 30 as will be described below in conjunction with FIG. 1C. In this position, the middle finger can be placed over depression 19 opposite the thumb placed on depression 18 and the remaining fingers wrap around back edge 16. The depressions 18 and 19 indicate the intended gripping technique making the proper handling of slitter 10 intuitive.

In one embodiment, major sides 6 and 8 are provided with a width W of approximately 1.7 inches at a widest point. Back edge 16 is provided with a length 9 along sloped portion 16a of approximately 1.4 inches. Handle 12 is provided with an overall thickness (not shown in the plan view of FIG. 1A but indicated by "T" in FIG. 5) of about 0.5 inches. While embodiments of handle 12 are not limited to these specific dimensions, these dimensions are illustrative of dimensions selected to comfortably accommodate a large range of user hand sizes. In particular, dimensions of handle 12 may be selected to accommodate hand sizes ranging from the fifth percentile of female hand sizes to the ninety-fifth percentile of male hand sizes. Hand size measured as the "grip width", across the palm of the hand along the metacarpal heads, ranges from about 2.7 inches for the fifth percentile of female hand sizes to 3.9 inches for the ninety-fifth percentile of male hand sizes. In embodiments intended to accommodate this range of hand sizes, the handle thickness may range from about 0.3 inches to 0.6 inches with the length of sloped portion 16a may be at least about one inch or more. The width W may be about 0.75 inches or more and will vary in part depending on the angle 7. The relatively large surface area of major sides 6 and 8 provides a large area for interfacing with a user's hand, allowing a secure comfortable grip for whole hand maneuvering of the slitter 10, and enhances the tactile feedback during use of the slitter 10.

Handle 12 is coupled to blade assembly 20 which includes a cutting blade 22 having an exposed, sharpened, forward-facing cutting edge 26 for slitting a guide catheter as it is withdrawn over slitter 10 as will be further described herein. Blade assembly 20 includes an upper portion 21 joined to and extending along handle lower edge 17. Blade assembly 20 further includes a shroud 28, extending substantially parallel to handle lower edge 17, below and behind blade 22. As will be described in greater detail herein, shroud 28 is designed to receive a segment of the body of an elongated medical device to stably maintain the longitudinal position of slitter 10 along the elongated device body. Shroud 28 protects the elongated device body from the cut edges of a slit guide catheter. Blade assembly 20 further includes a nose piece 24 which becomes positioned between the elongated device body and the inner surface of the guide catheter and acts to direct the guide catheter wall against cutting edge 26.

Holding mechanism 30 includes an actuator 32 and a retaining finger 34 coupled to the actuator 32. A lateral arm 36 extending between the actuator 32 and the retaining finger 34 couples retaining finger 34 to actuator 32 and causes retaining finger to move from a closed position to an open position upon activation of actuator 32. In the embodiment shown, actuator 32 is depressed toward and into handle 12, in the direction indicated by arrow 29a, to cause lateral displacement of arm 36 and retaining finger 34.

FIG. 1B is a side plan view of slitter 10 upon actuation of holding mechanism 30 to an open position. In response to depression of actuator 32, lateral arm 36 and retaining finger 34 are laterally displaced along an axial direction with respect to shroud 28, as indicated by the arrow 29b, to an open position as shown in FIG. 1B. As used herein, "axial direction" refers to a direction generally corresponding to a central axis of the shroud 28 or an axis extending substantially parallel thereto. The term "perpendicular direction" refers to any direction substantially perpendicular to the central axis of the shroud. A tip 33 of retaining finger 34, visible in the open position shown in FIG. 1B, is axially centered along shroud 28 such that in the closed position shown in FIG. 1A, retaining finger 34 retains the elongated device body within shroud 28. Lateral arm 36 is axially offset from retaining finger 34 and shroud 28 such that the elongated body can extend through shroud 28 and along retaining finger top edge 37, which acts as a passive guide to the elongated body as it extends away from slitter 10.

Figure 1C:
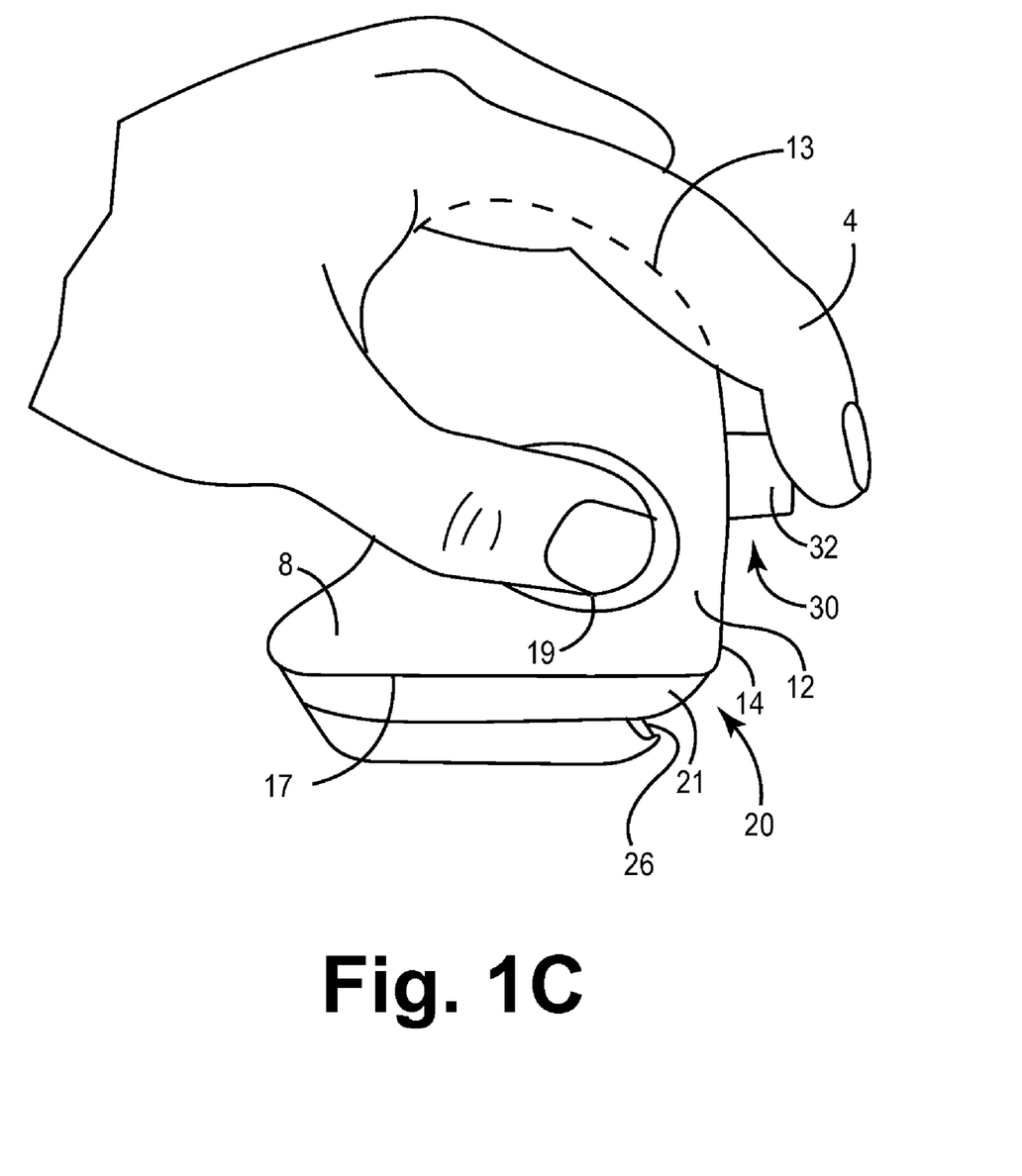
FIG. 1C illustrates a user holding a slitter in a position for actuating a holding mechanism.

FIG. 1C illustrates a user holding slitter 10 in a position for actuating the holding mechanism 30. A user's forefinger 4 extends along the top arcuate edge 13 and forward edge 14 of handle 12. Actuator 32 is readily depressed by forefinger 4 to cause lateral displacement of the retaining finger 34 (not visible in the view of a left-handed grasp shown in FIG. 1C) to the open position as shown in FIG. 1B. The shape and size of handle 12 allows a one-handed, substantially whole-handed grip to remain secure during activation of actuator 32.

Forward edge 14 and lower edge 17 meet at an approximately ninety degree angle and depressions 18 and 19 are located along a generally forward portion of major sides 6 and 8. This particular arrangement of slitter handle features allows the user to grip handle 12 near the blade assembly and to hold slitter 10 in a stable position near the crucial interaction points of the cutting edge 26 and the actuator 32, without obscuring the line of sight of these interaction points.

Furthermore, multiple slitter features provide visual indicators of the intended grasping method and orientation of handle 12 relative to a guide catheter. For example, the horizontal lower edge 17 is optimally held substantially parallel to the guide catheter body being slit. Upper portion 21 of blade assembly 20 and handle 12 may be formed of materials having contrasting colors such that the horizontal lower edge 17 is a visually distinct indicator of the intended parallel slitter alignment with the guide catheter. In one embodiment, blade assembly 20 is formed from a black material and handle 12 is formed from a white, blue, red, yellow or any other contrasting color. Actuator 32 extends horizontally from slitter forward edge 14, parallel to horizontal lower edge 17, thereby providing another visual indicator for promoting horizontal alignment of slitter handle lower edge 17 with the guide catheter. The perpendicular intersection of forward edge 14 and lower edge 17 provides another alignment feature for proper orientation of the slitter relative to the guide catheter. These visual alignment features increase the likelihood of horizontal and axial alignment of handle lower edge 17 with the guide catheter promoting proper use of the slitter and thereby reducing the likelihood of damage or breakage of the guide catheter, the slitter, and the elongated body extending within the guide catheter due to improper pitch, roll or yaw of the slitter relative to the guide catheter.

Figure 2:
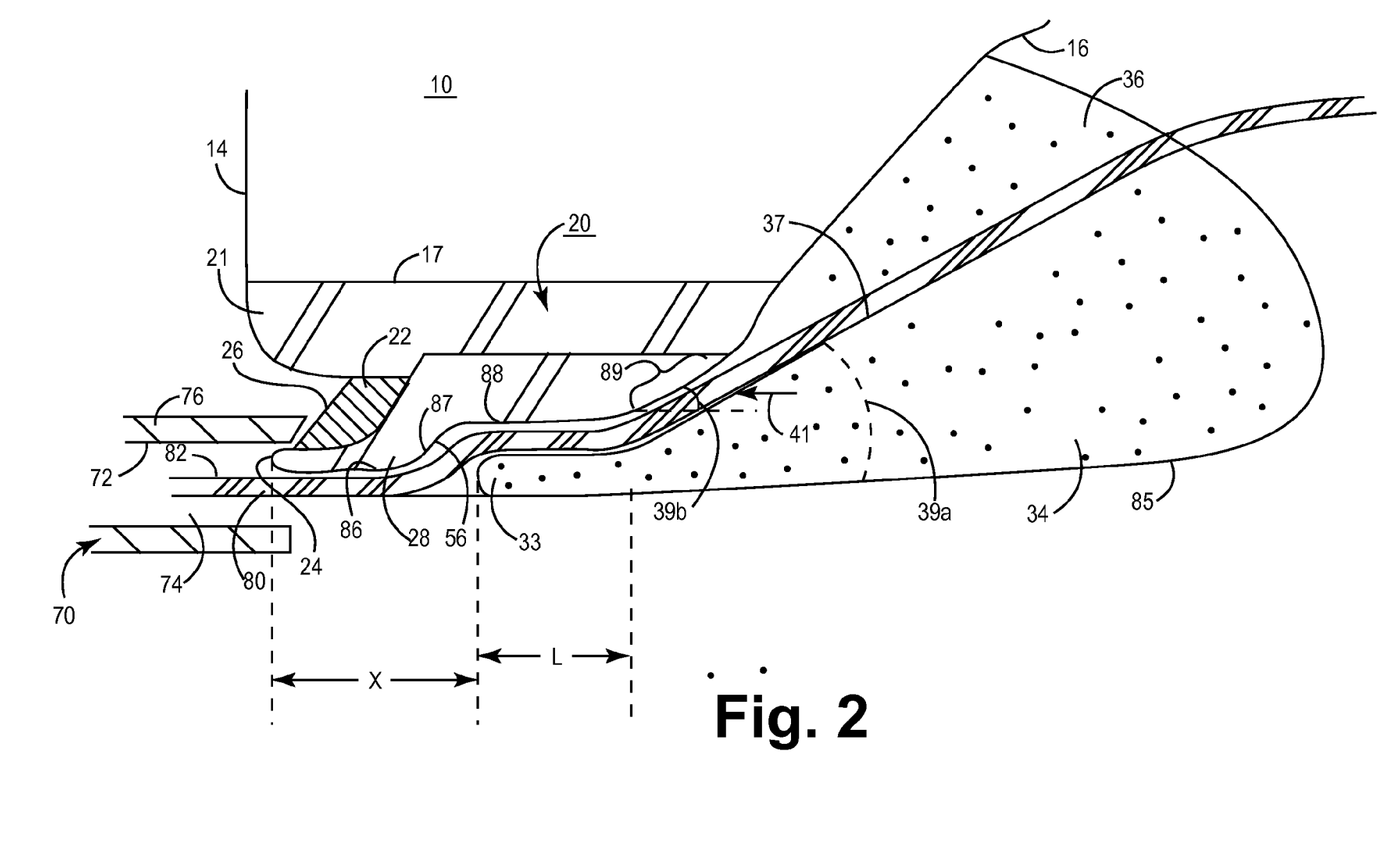
FIG. 2 is an enlarged sectional view of a slitter showing the position of an elongated device body and guide catheter as the guide catheter is advanced over the slitter.

FIG. 2 is an enlarged sectional view of slitter 10 showing the position of an elongated device body 80 and guide catheter 70 as guide catheter 70 is advanced toward cutting edge 26. Guide catheter 70 includes an open lumen 74 formed by inner surface 72 through which the elongated device body 80 extends. Nose piece 24 is positioned between the inner surface 72 of guide catheter 70 and an outer surface 82 of elongated body 80. Guide catheter wall 76 is then slit open over cutting edge 26 as guide catheter 70 is withdrawn over elongated body 80 and passed along blade assembly 20. Elongated body 80 extends through shroud 28 and along retaining finger top edge 37. Retaining finger 34, shown in a closed position, retains elongated body 80 within shroud 28.

When the holding mechanism 30 is activated as shown in FIG. 1B, the retaining finger 34 is moved laterally away from shroud 28, along an axial direction with respect to shroud 28, to the open position, allowing the elongated body 80 to be slipped out of shroud 28 and off retaining finger top edge 37, thereby allowing slitter 10 to be removed from the elongated device body 80.

Shroud 28 includes a groove 56 for receiving the elongated device body 80. The inner contour of groove 56 of shroud 28 is shown in the sectional view of FIG. 2. Groove 56 includes a distal portion 86 extending proximally from a point beneath and proximate nose 24 to a distal sloped portion 87. As used herein the term "distal" refers to a generally "forward" direction corresponding to nose 24, cutting edge 26 and front handle edge 14. The term "proximal" refers to a direction generally corresponding to back handle edge 16. Groove 56 is relatively shallow along distal portion 86, however, groove 56 is formed deeper by distal sloped portion 87, thereby allowing elongated body 80 to extend well within shroud 28. In this way, elongated body 80 can be stably retained within, and be protected by, shroud 28. Distal sloped portion 87 extends from distal portion 86 to an intermediate portion 88 that extends substantially horizontally, i.e. parallel to handle lower handle edge 17, between distal sloped portion 87 and a proximal sloped portion 89.

Top edge 37 of retaining finger 34 is sloped to interface with the proximal sloped portion 89 of groove 56. Elongated device body 80 becomes impinged between top edge 37 and shroud groove 56 along proximal sloped portion 89. In the embodiment shown, retaining finger bottom edge 85 extends horizontally, i.e. substantially parallel to handle lower edge 17. Retaining finger top edge 37 slopes at an angle 39a relative to bottom edge 85. The angle 39a of sloped top edge 37 is selected to allow secure impingement of the elongated body 80 extending through groove 56 without kinking or damaging elongated body 80. In one embodiment, the angle 39a of sloped top edge 37 is about twenty to thirty degrees, though embodiments of the invention are not limited to any particular angle. For example, angle 39a may be ninety degrees or more, however, such angles may introduce greater potential for kinking of elongated body 80 as it extends along top edge 37 of retaining finger 34. Angle 39a may be less than twenty degrees, however as top edge 37 becomes flat, i.e. approaches a horizontal configuration, the impingement of the elongated body 80 within groove 56 may become less secure, potentially allowing slippage of slitter 10 along elongated body 80. Greater lateral displacement of the retaining finger 34 may also be required to move a flat retaining finger 34 away from shroud 28 to an open position.

While the angle 39a of sloped top edge 37 is shown relative to a substantially horizontal bottom retaining finger edge 85, it is recognized that bottom edge 85 need not be horizontal. The slope of top edge 37 relative to the contour of shroud groove 56 will determine the location and distance along elongated body 80 and groove 56 that elongated body 80 becomes impinged between retaining finger 34 and groove 56. As shown in FIG. 2, groove 56 includes proximal sloped portion 89 that angles upward at angle 39b to interface with sloped top edge 37 of retaining finger 34. Angle 39b of proximal sloped portion 89 does not need to exactly match angle 39a of retaining finger sloped top edge 37, however, an approximate correspondence between these angles and slopes allows retaining finger 34 to securely hold elongated body 80 within groove 56 without kinking or damaging body 80.

When a spring-loaded actuator, used to displace retaining finger 34 to an open position, is released, retaining finger 34 springs forward as indicated by arrow 41 such that elongated body 80 becomes impinged within groove 56 along sloped proximal portion 89. Retaining finger 34 may be provided with a tip 33 extending distally (toward nose 24) from retaining finger 34. Tip 33 supports the elongated body 80 along horizontal portion 88 of groove 56 such that body 80 does not fall out of shroud 56 and minimizes the potential of buckling of elongated body 80. Retaining finger tip 33 may be formed with a length L selected to minimize the distance X between nose 24 and finger tip 33 such that the distance X of an unsupported length of elongated body 80 between nose 24 and finger tip 33 is minimized. In one embodiment, finger tip 33 is approximately 0.20 inches in length.

Elongated body 80 is held securely within slitter 10 without requiring the user to hold or grip elongated body 80. A user may choose, however, to grasp elongated body 80 using his/her fingers wrapped around back edge 16 of the slitter handle 12. Elongated body would extend along a portion of top edge 37 then extend along back edge 16, held in place by the user's fingers. The length 9 of sloped portion 16a of back edge 16 (as shown and described in conjunction with FIG. 1A) allows the user to grasp the elongated body 80 between the handle and his/her fingers, thereby providing greater tactile feedback and confidence to the user that the elongated body 80 is held securely and not being shifted or dislodged.

Figure 3A:
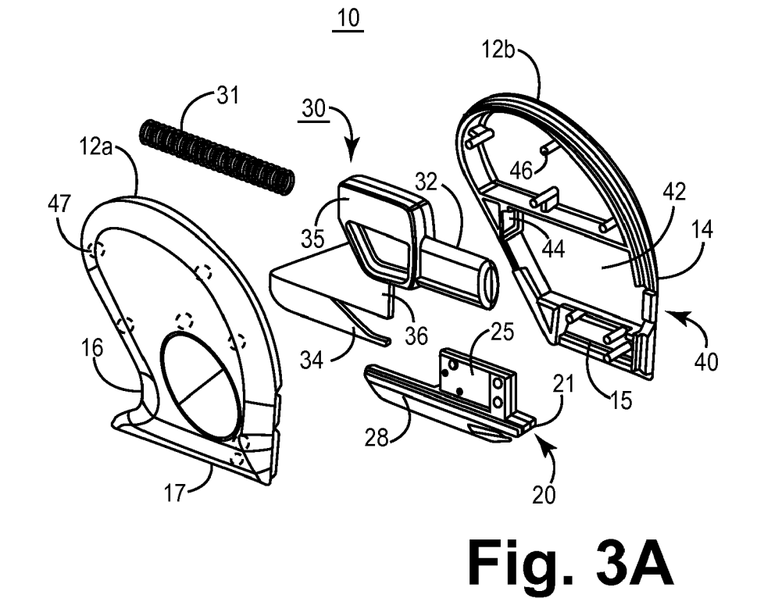
FIG. 3A is an exploded view of a slitter.

FIG. 3A is an exploded view of slitter 10. Handle 12 is an assembled component formed from interlocking opposing portions 12a and 12b. Portions 12a and 12b are formed with interlocking features, such as pegs 46 in portion 12b and corresponding receptacles 47 (indicated by dashed circles) in portion 12a, which may engage to form a snap fit assembly. In alternative embodiments, assembly of portions 12a and 12b may include the use of an adhesive or other mechanical, chemical or thermal joining methods. When assembled together by mating interlocking features 46 and 47, opposing portions 12a and 12b form a cavity 42 for housing a body 35 of holding mechanism 30. Handle 12 is made relatively large to provide a secure, comfortable grip, using more of a "whole hand" grip rather than a grip using only the thumb and one or two fingers as in past practice. In other words, the overall size of handle 12 allows the handle to rest in the palm of the user's hand while grasping handle 12 with the thumb and up to all four fingers. In making handle 12 relatively large, for example according to the dimensions specified above, the assembly of the handle 12 from piece parts, namely portions 12a and 12b, allows handle 12 to be hollow and remain relatively lightweight. Furthermore, by forming a hollow handle having cavity 42 allows moving parts of holding mechanism 30 to be present within handle 12. This ability to contain moving parts within handle 12 is in contrast to solid handles formed in past practice, for example by overmolding a slitting blade, which preclude the assembly of moving parts within the handle.

Holding mechanism body 35 couples lateral arm 36 and actuator 32. Body 35 is positioned in cavity 42 with actuator 32 extending out of handle 12 through opening 40 along forward edge 14. Cavity 42 includes a spring interface 44 for supporting a spring 31 assembled in holding mechanism body 35. As such, holding mechanism 30 is provided as a spring-loaded mechanism. Depression of actuator 32 in the direction of rear handle edge 16 displaces retaining finger 34 to an open position and causes compression of spring 31 against spring interface 44. Retaining finger 34 is returned to a normally closed position by the action of spring 31 returning to a normal position upon release of actuator 32.

As used herein, the term "normal position" with reference to a spring mechanism included in holding mechanism 30 refers to a position of the spring when the retaining finger is in a normal position, which may be an open or closed position but is typically a closed position. The "normal position" of the spring 31, therefore, may be the spring equilibrium position but is not necessarily the spring equilibrium position and may be a position of slight tension or compression. The "normal position" of spring 31 is at least closer to the spring equilibrium position than the spring position during activation of the actuator 32. In the embodiment shown, the "normal position" of spring 31 associated with retaining finger 34 in a normally closed position corresponds to a position that is less compressed, i.e. closer to an equilibrium position, than during activation of actuator 32. The spring position when the retaining finger 34 is moved to an open position by actuator 32 is a more compressed position than the normal, slightly compressed position.

Handle 12 further includes a chassis 15 upon which a coupling portion 25 extending upward from blade assembly upper portion 21 is mounted during assembly of slitter 10 to thereby securely join blade assembly 20 to handle 12 along handle lower edge 17. Handle portions 12a and 12b may be formed as molded parts fabricated from, but not limited to, a polycarbonate material, such as RTP 301Z available from RTP Company, Winona, Minn. Holding mechanism 30 may be formed from a rigid polymer such as, but not limited to, a styrene material, for example RTP 600 available from RTP Company. Blade assembly 20 may be formed as a molded component formed from, but not limited to, a nylon resin such as Zytel 70G33L available from DuPont, Wilmington, Del. The cutting blade 22 mounted in blade assembly 20 is formed, for example, from stainless steel with a beveled edge to from a sharp cutting edge 26. Cutting blade 22 may be formed from other durable metals, coated metals, ceramic materials, cermets, or rigid polymer materials.

Figure 3B:
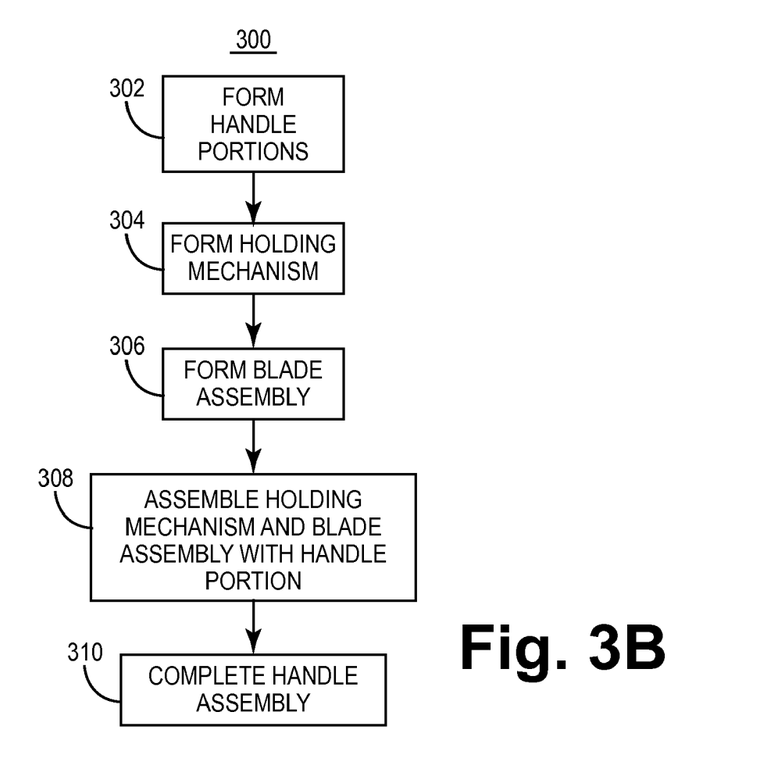
FIG. 3B is a flow chart of a method for manufacturing a slitter.

FIG. 3B is a flow chart of a method 300 of manufacturing a slitter, for example slitter 10 shown in FIG. 3A. Handle portions 12a and 12b are formed as molded or machined piece parts at block 302. The holding mechanism 30 is formed as a molded or machined part or as an assembled component at block 304. The blade assembly 20 is formed at block 306 by overmolding the slitting blade 22, e.g., using an injection molding process. The holding mechanism 30 and blade assembly 20 are assembled with a handle portion 12b at block 308. For example, with reference to FIG. 3A, the coupling portion 25 of the blade assembly 20 may be mounted on chassis 15 of handle portion 12b. The holding mechanism may then be assembled along blade assembly 20 and cavity 42 of handle portion 12b and spring 31 inserted into the holding mechanism body 35 and against spring interface 44. At block 310, the handle assembly is completed. In the embodiment shown in FIG. 3A, opposing handle portion 12a is snapped together with handle portion 12b by mating interlocking features 46 and 47.

Figure 4:
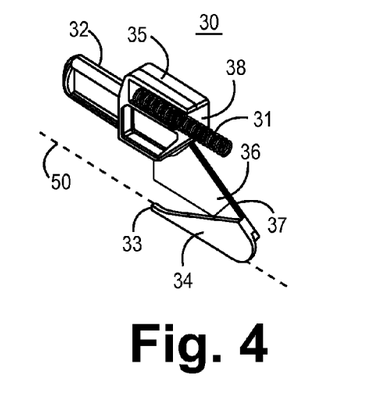
FIG. 4 is a perspective view of a holding mechanism included in the slitter shown in FIG. 3A.

FIG. 4 is a perspective view of the holding mechanism 30. Holding mechanism body 35 is shown in this view having a spring receptacle 38 in which spring 31 is assembled. As can be seen in this perspective view, lateral arm 36 is axially offset from retaining finger 34. Axis 50, shown in dashed line, indicates the approximate position of a central axis of shroud 28 through which an elongated device body will be positioned during guide catheter slitting. Retaining finger 34 is centrally aligned with axis 50, whereas lateral arm 36 is offset from axis 50. This positioning of lateral arm 36 relative to retaining finger 34 allows retaining finger 34 with tip 33 to be aligned along a central axis 50 of shroud 28 without impingement of the elongated device body by lateral arm 36. The elongated body can extend along retaining finger top edge 37, as shown in FIG. 2, adjacent arm 36.

Figure 5:
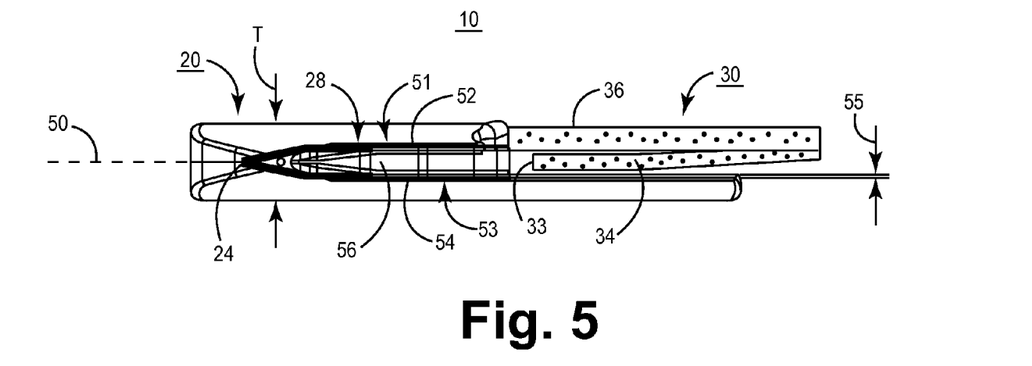
FIG. 5 is a bottom view of a blade assembly included in the slitter of FIG. 3A, showing a portion of a holding mechanism in an open position.

FIG. 5 is a bottom view of blade assembly 20 showing a portion of holding mechanism 30 in an open position. A thickness T is shown indicating an overall thickness of the slitter, including the thickness of handle 12 described previously in conjunction with FIG. 1A. Shroud 28 includes opposing flanges 52 and 54 forming a groove 56 therebetween for receiving an elongated device body. Shroud 28 begins proximate nose 24 and may extend any portion of the length of blade assembly 20. Flanges 52 and 54 are formed as very thin sidewalls of groove 56 such that flanges 52 and 54 can flex. Thin flanges 52 and 54 can flex in response to the cut edges of the guide catheter being withdrawn over blade assembly 20. The cut edges of the guide catheter will impart inward pressure against outer surfaces 51 and 53 of flanges 52 and 54 causing flanges 52 and 54 to flex inward. For example each flange may be formed having a thickness 55 of less than 0.02 inches. In one embodiment, flanges 52 and 54 formed from Zytel 70G33L have a thickness of approximately 0.010 to 0.012 inches.

Holding mechanism 30 is shown in an open position wherein lateral displacement of lateral arm 36 moves retaining finger 34 away from shroud 28 allowing an elongated body to be placed into shroud 28 or removed from shroud 28. Upon release of the actuator (not shown in FIG. 5), tip 33 of retaining finger 34 will advance axially in the direction of nose 24 over groove 56, substantially along central axis 50 of shroud 28, thereby retaining an elongated body that has been positioned within groove 56. By providing retaining finger 34, which impinges an elongated body within groove 56, as described in conjunction with FIG. 2, shroud 28 can be formed with a relatively wide groove 56 and still securely retain a range of elongated device body diameters therein.

Figure 6:
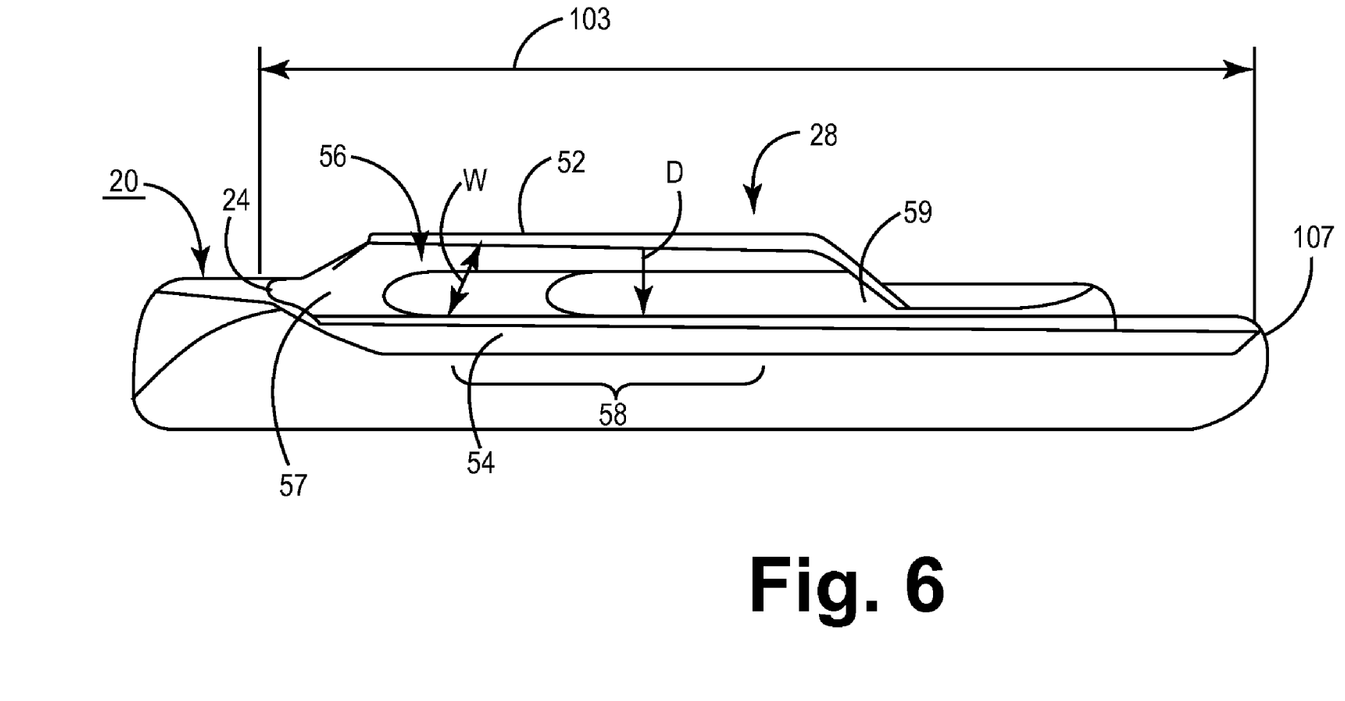
FIG. 6 is a bottom perspective view of the shroud included in the blade assembly of FIG. 5.

FIG. 6 is a bottom perspective view of shroud 28 of blade assembly 20. Shroud 28 is formed such that groove 56 formed by flanges 52 and 54 gradually deepens moving from a distal area 57, proximate nose piece 24, to a proximal area 58. By forming groove 56 relatively deep along the proximal area 58, for example having a depth D that is greater than the width W between flanges 52 and 54 when the flanges are in an unflexed position, the inward flexion of flanges 52 and 54 can be increased when an elongated body is held in groove 56 and a guide catheter is withdrawn over the slitter. In one embodiment the width W between opposing flanges 52 and 54 in an unflexed position is approximately 0.07 to 0.1 inches and the depth D of groove 56 is variable with the greatest depth being 0.1 inches or more. Flange 52 tapers upward toward the slitter handle at proximal end 59. As shown previously in FIG. 2, the elongated device body would flex upward as it exits shroud 28 and rest along the retaining finger top edge 37 (not shown in FIG. 6). Flange 54 may extend further proximally to support the displaced retaining finger 34 upon actuation of holding mechanism 30 (not shown in FIG. 6).

By forming groove 56 relatively deep along proximate portion 58 and forming flanges 52 and 54 very thin, shroud 28 is a "collapsible" shroud in that it will naturally flex inward around an elongated body extending there through in response to the cut walls of the guide catheter applying external pressure to the flanges 52 and 54. As such, a range of elongated body outer diameters can be accommodated by shroud 28. The elongated body is securely held and protected by flanges 52 and 54, reducing the risk of device movement or damage. As flanges 52 and 54 flex inward around the elongated body, the guide catheter encounters a narrower profile over which it must pass as it is being advanced over the slitter. Accordingly, smaller diameter guide catheters, such as 4 French guide catheters can be easily passed over a slitter having a collapsible shroud 28.

The length 103 between nose 24 and proximal end 107 of blade assembly 20 is approximately 1.5 inches or more in one embodiment. The cut edges of a guide catheter being slit over blade assembly 20 will remain engaged with blade assembly 20 along the entire, or at least a majority of, length 103. This relatively long length of engagement between the guide catheter and the slitter promotes smooth advancement of the slitter through the guide catheter as varying resistances are encountered, requiring varying applied force to slit the catheter. For example, a proximal hub is often present on a guide catheter proximal end. The hub, the junction between the hub and the guide catheter body and the guide catheter body itself are each characterized by different slitting resistances due to the different thicknesses and materials of these zones. A user withdrawing a guide catheter over the slitter will need to apply different forces to the slitter as it passes each of these zones, i.e. the hub, the junction, and the body.

The greatest slitting resistance is typically encountered along the junction where the hub and the guide catheter body overlap. The user will have a tendency to apply greater force to the slitter as the hub and hub/body junction are slit open. Upon reaching the guide catheter body, a sudden decrease in slitting resistance tends to cause the slitter to lurch forward relative to the guide catheter body, which can cause the slitter and guide catheter to become disengaged or cause undesired movement of the elongated device body. The relatively long length 103 of blade assembly 20 acts as a brake to prevent sudden lurching of the slitter relative to the guide catheter and provide a smooth transition of required force applied to the slitter as different material slitting resistances are encountered.

Figure 7:
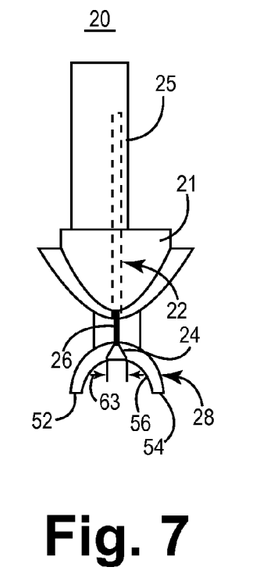
FIG. 7 is a front view of a blade assembly included in a slitter.

FIG. 7 is a front view of blade assembly 20. Blade assembly coupling portion 25 extends upward from the upper portion 21 of blade assembly 20. Blade 22 is mounted within coupling portion 25 and upper portion 21 and is exposed above nose 24 and shroud 28 to form cutting edge 26. Shroud 28 includes flanges 52 and 54 forming a groove 56 there between for receiving an elongated device body. Nose 24 is shown having a generally triangular cross-section. In one embodiment, nose 24 is provided with a maximum width 63 of about 0.035 inches or less. The generally triangular cross-section and relatively small size of nose 24 in comparison to nose pieces used in past practice promotes alignment of a guide catheter wall against cutting edge 26 with reduced risk of breakage or damage to the slitter 10 or to the guide catheter or elongated device body.

Figure 8:
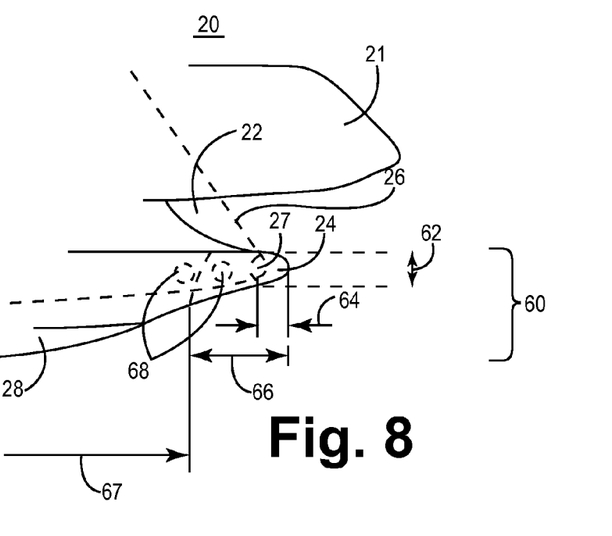
FIG. 8 is an enlarged side view of a forward portion of a blade assembly.

FIG. 8 is an enlarged side view of a forward portion of blade assembly 20. The exposed portion of blade 22 is shown forming cutting edge 26. Nose 24 extends forward from cutting edge 26 to direct a guide catheter wall against edge 26 (as previously illustrated and described in conjunction with FIG. 2). However, nose 24 is provided with relatively small dimensions compared to nose pieces provided on slitters in past practice. In one embodiment, nose 24 is provided with a height 62 of about 0.035 inches or less, and extends a maximum distance 64 of about 0.035 inches or less from cutting edge 26. The relatively short nose 24 imparts less leverage than a longer nose would when the slitter is held at a downward angle, or in a "nose down position", rather than substantially parallel and level with the guide catheter outer surface. The relatively short nose 24 thus reduces the likelihood of the nose piece 24 breaking off or separating from blade 22. The relatively small dimensions in height 62 and width 63 (FIG. 7) and generally triangular shape of nose 24 further promote smooth cutting of the guide catheter wall over cutting edge 26 by reducing the likelihood of ripping or breaking the guide catheter, even when the slitter is held in a "nose down" position.

Blade 22, as shown by dashed line, extends through the upper portion 21 of blade assembly 20 as well as a lower portion 60, which extends below exposed cutting edge 26, and forms nose 24 and shroud 28. In various embodiments, the blade 22 and nose 24 are designed to prevent breakage or separation of nose 24 from blade 22. Blade 22 may be provided with one or more features for enhancing the mechanical engagement between blade 22 and the material used to form blade assembly 20. In one embodiment, blade 22 is provided with one or more cut-outs 68 through the portion of blade 22 located in lower portion 60 of blade assembly 20. During a manufacturing process, the blade assembly 20 is formed by over molding blade 22 with a polymer material in an injection molding process. The polymer material can flow through cut-outs 68 to form a mechanical interlock between blade 22 and the polymer material forming blade assembly 20. Blade 22 may also be designed with a geometry that extends as far into nose piece 24 as possible to minimize the unsupported length of nose 24. However, blade 22 may be provided with a distal notch 27 to minimize the likelihood of blade 22 cutting through nose 24.

In other embodiments, nose piece 24 may be formed from a different material than the remainder of lower portion 60 in a two shot over molding process. For example, nose piece 24 may be formed by injection molding a polymer that forms a rigid forward portion 66 along blade assembly lower portion 60. The material selected to form nose piece 24 (and/or other portions of blade assembly 20) may be a material, such as an epoxy, that forms a chemical bond to the blade material. A rear section 67 of lower portion 60 may be formed of a relatively less rigid polymer, having a lower Shore hardness, such as a polypropylene material, in a separate injection molding step to form shroud 28. The lower portion 60 may be formed in a two-step process to provide different material properties in nose piece 24 than in shroud 28. For example, by providing a rigid, mechanically interlocking forward portion 66, the coupling between nose piece 24 and blade 22 may be made durable while a more flexible material may be used to form a collapsible shroud 28 capable of flexing around an elongated device body.

Figure 9:
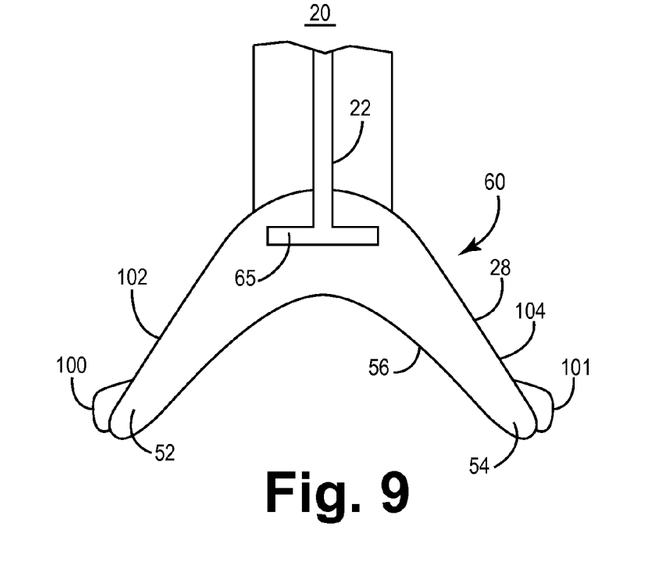
FIG. 9 is an enlarged, sectional view of a forward portion of a blade assembly according to an alternative embodiment.

FIG. 9 is an enlarged, sectional view of a forward portion of a blade assembly 20 according to an alternative embodiment. Blade 22 extends into lower portion 60 of blade assembly 20 which forms nose 24 (not shown in this sectional view) and shroud 28. Blade 22 may be provided with one or more flanges 65 extending outward from blade 22 within lower portion 60 to enhance the durability of the mechanical coupling between the blade 22 and the lower portion 60 of the blade assembly 20. Flange 65 may be formed by bending blade 22 outward, welding a separate metal piece to the lower edge of the blade 22 or anchoring a metal strip or wire through a cut-out formed in blade 22. Flange 65 may extend outward from blade 22 in one or more directions and provides additional surface area for mechanically joining the blade 22 to the polymer material forming lower portion 60. The surface of blade 22 may also be enhanced to promote bonding between the material used to form blade 22 and the polymer used to form lower portion 60. Surface enhancements may include mechanical or chemical roughening or providing a coating that promotes chemical bonding.

Blade assembly 20 may further include catheter guide rails 100 and 101 as generally disclosed in co-pending U.S. patent application Ser. No. 11/844,912, incorporated herein by reference in its entirety. Catheter guide rails 100 and 101 are shown extending laterally outward from outer surfaces 102 and 104 of flanges 52 and 54, respectively. Guide rails 100 and 101 direct the cut walls of the guide catheter being slit by cutting edge 26 over the slitter and help to maintain a proper position of the guide catheter relative to the cutting edge of blade assembly 20. The guide catheter engagement with the slitter is better maintained by the guide rails, which act to prevent the catheter from falling off the slitter. The guide rails also provide resistance against angling the slitter in a "nose-down" position and thereby promote maintenance of a substantially parallel orientation between the slitter lower edge 17 (not seen in FIG. 9) and the guide catheter outer surface.

The guide catheter cut edges may apply pressure along the outer surfaces 102 and 104 of flanges 52 and 54 thereby causing inward flexion of flanges 52 and 54 (toward each other) around an elongated device body extending through groove 56. This additional pressure applied to the outer surfaces 102 and 104 by the cut guide catheter walls may therefore contribute to stably retaining the elongated device body within shroud 28.

Figure 10A:
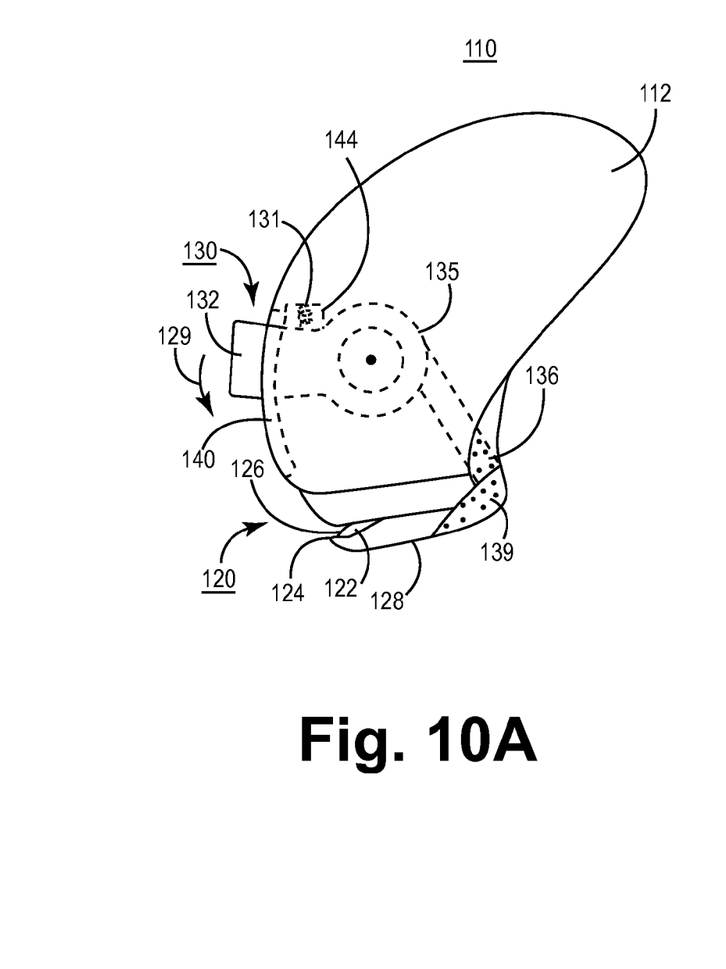
FIGS. 10A and 10B are plan views of an alternative embodiment of a slitter having a holding mechanism shown in closed and open positions, respectively.
Figure 10B:
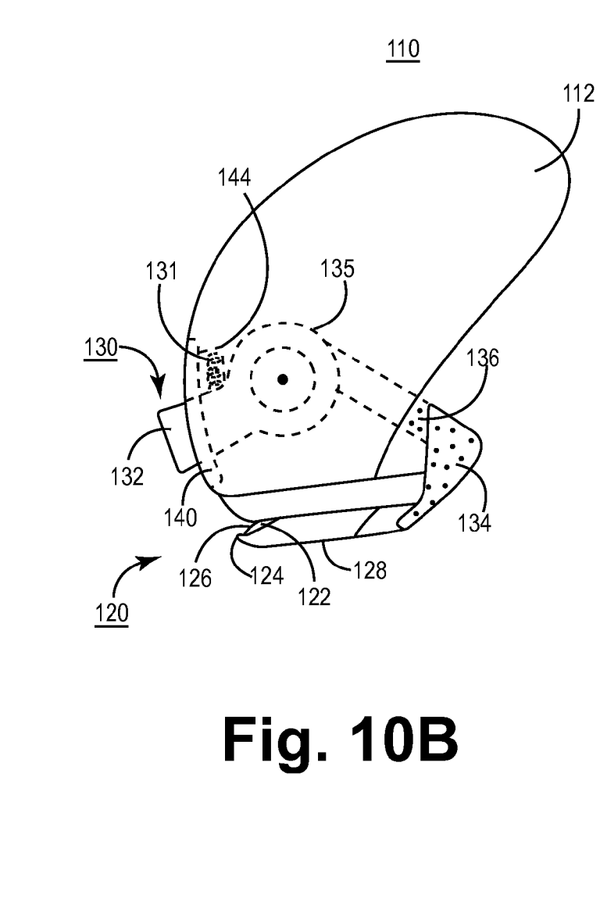

FIGS. 10A and 10B are plan views of an alternative embodiment of a slitter having a holding mechanism shown in closed and open positions, respectively. It is recognized that various actuator mechanisms and configurations may be conceived for displacing a mechanical holding finger from a closed position over the shroud to an open position. In FIG. 10A, slitter 110 includes handle 112, holding mechanism 130, and blade assembly 120. Holding mechanism 130 includes an actuator 132 coupled to a wheel 135 mounted rotatably within hollow handle 112. Lateral arm 136 couples retaining finger 134 to wheel 135 and actuator 132. Downward depression of actuator 132 in the direction indicated by arrow 129 along opening 140 in handle 112 causes rotation of wheel 135 and upward, rotational displacement of lateral arm 136 and retaining finger 134 to the open position shown in FIG. 10B. The rotational displacement occurs along an axial direction with respect to shroud 128

In the closed position shown in FIG. 10A, retaining finger 134 is centrally aligned along shroud 128 to hold an elongated body within shroud 128. A guide catheter is slit over cutting edge 126 of blade 122 as it is withdrawn over nose piece 124 and blade assembly 120 as generally described above. The elongated body can be removed from shroud 128 upon displacement of retaining finger 134 to the open position shown in FIG. 10B.

Holding mechanism 130 is shown as a spring-loaded system including spring 131 coupled between an interface 144 of handle 112 and actuator 132. Spring 131 is at its normal position, which may be an equilibrium position or a position of slight tension, when retaining finger 134 is in a closed position as shown in FIG. 10A. Spring 131 is stretched as actuator 132 is pressed downward to move retaining finger to an open position as shown in FIG. 10B. As such, retaining finger 134 will return to a normally closed position upon release of actuator 132 as spring 131 returns to its normal position. While holding mechanisms 30 (shown in FIG. 3A) and 130 described herein have been illustrated as spring-loaded mechanisms, a holding mechanism may alternatively be provided having a bistable actuator that is actively moved by the user between two states for displacing the retaining finger between open and closed positions.

Figure 11A:
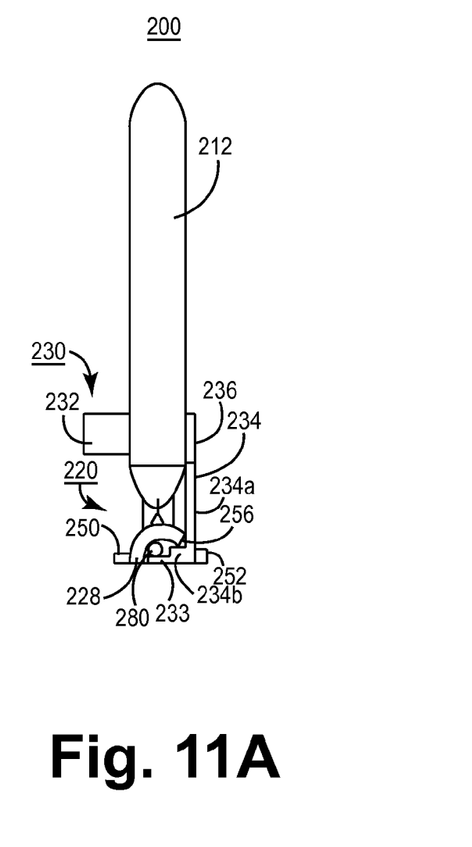
FIG. 11A is a front plan view of a slitter according to an alternative embodiment.

FIG. 11A is a front plan view of a slitter 200 according to an alternative embodiment. Slitter 200 includes a handle 212 coupled to a blade assembly 220 and a holding mechanism 230. The holding mechanism 230 includes an actuator 232 coupled to a retaining finger 234 via a lateral arm 236. Retaining finger 234 includes a longitudinal portion 234a extending between lateral arm 236 and a lateral portion 234b. Lateral portion 234b is configured to retain an elongated device body 280 within groove 256. Elongated device body 280 becomes impinged between groove 256 and lateral portion 234b when retaining finger 234 is in a closed position. An optional finger tip 233 extends from retaining finger 234 and is axially aligned with groove 256 to support elongated device body 280 from underneath within groove 256.

In this embodiment, one guide rail 250 may be formed along an outer surface of the shroud 228 and a second guide rail 252 may be formed along an outer surface of the retaining finger 234 to engage the cut walls of a guide catheter being slit open by slitter 200.

Figure 11B:
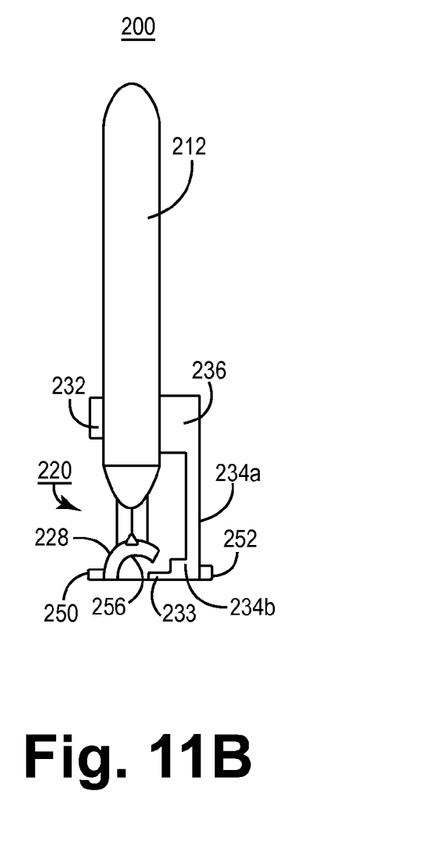
FIG. 11B is a front plan view of the slitter of FIG. 11A during activation of a holding mechanism actuator.

FIG. 11B is a front plan view of the slitter 200 of FIG. 11A during activation of actuator 232. Depression of actuator 232 causes lateral displacement of lateral arm 236, thereby causing lateral displacement of retaining finger 234. Lateral movement of retaining finger 234 away from shroud 228 allows an elongated device body to be positioned in or removed from groove 256. The lateral displacement occurs in a direction perpendicular to the shroud axis in this embodiment rather than in an axial direction relative to shroud 228 as described in previous embodiments.

In various embodiments, a holding mechanism, having a retaining finger axially aligned along a shroud in a closed position, may be configured for lateral or rotational displacement from the closed position to an open position. The lateral or rotational displacement may be along an axial direction with respect to the shroud or in a perpendicular direction with respect to the shroud. The perpendicular displacement may be along any radius extending outward from an axis of the shroud, including a downward direction away from the slitter lower edge. It is recognized that numerous variations may be conceived by one having skill in the art and the benefit of the teachings provided herein for implementing a retaining finger that is axially aligned with a shroud groove in a first position associated with retaining an elongated body within the groove and displaced from that first retaining position to a second open position for releasing the elongated body from the shroud groove.

The displacement between open and closed positions of a retaining finger may be caused by a user-activated actuator, which may be a spring-loaded mechanism as described herein. It is recognized that a spring-loaded holding mechanism may include a tensional spring, torsional spring, compression spring, coil (helical) spring, conical spring, Belleville spring, or other spring mechanism that produces a force for returning the retaining finger to a normal position upon release of the actuator. Furthermore, the normal position of a retaining finger may be an open position corresponding to releasing an elongated body from the shroud or a closed position corresponding to retaining the elongated body within the shroud. As such, the actuator may be implemented such that a user continues activating the actuator in order to retain an elongated body in the slitter throughout the slitting procedure. Upon releasing the actuator, the retaining finger returns to a normally open position for releasing the elongated device body.

Thus, a slitter for use in removing a guide catheter from an elongated medical device body has been presented in the foregoing description with reference to specific embodiments. It is appreciated that various modifications to the referenced embodiments may be made without departing from the scope of the invention as set forth in the following claims.

The invention claimed is:

1. A slitter for slitting a guide catheter, comprising:
 a handle;
 a blade assembly coupled to the handle comprising a shroud for receiving an elongated body of a medical device, a slitting blade having an exposed cutting edge, and a nose piece extending forward of the cutting edge, wherein the shroud defines a groove comprising at least a first groove portion and a second groove portion, the first groove portion being proximate the nose piece extending along an axis and configured to receive a first portion of the elongated body along the axis, and further wherein the second groove portion is proximal to the first groove portion; and
 a holding mechanism coupled to the handle, the holding mechanism comprising:
  an actuator; and
  a retaining finger coupled to the actuator and extending along at least a portion of the second groove portion defined by the shroud, wherein the retaining finger is configured to guide at least a second portion of the elongated body proximal the first portion of the elongated body away from the axis and retain at least the second portion of the elongated body within at least the second groove portion defined by the shroud between the retaining finger and the shroud when the retaining finger is in a closed position.

2. The slitter of claim 1 wherein the retaining finger is movable between a normally closed position for retaining the elongated body in the shroud and an open position for releasing the elongated body from the shroud in response to activation of the actuator.

3. The slitter of claim 2 wherein the retaining finger is movable in one of an axial direction with respect to the shroud and a perpendicular direction with respect to the shroud.

4. The slitter of claim 2 wherein activation of the actuator causes one of lateral displacement and rotational displacement of the retaining finger between the open position and the closed position.

5. The slitter of claim 2 wherein the holding mechanism further comprises a spring mechanism being displaced from the normally closed position upon activation of the actuator.

6. The slitter of claim 2 wherein the holding mechanism further comprises a lateral arm coupling the actuator to the retaining finger.

7. The slitter of claim 6 wherein the retaining finger comprises a tip having a length that is axially aligned with the axis of the shroud, the lateral arm being axially offset from the retaining finger.

8. The slitter of claim 2 wherein the holding mechanism further comprises a rotatable member coupled between the retaining finger and the actuator,
 the rotatable member and the actuator are configured to cause rotational displacement of the retaining finger between the closed position and the open position in response to activation of the actuator.

9. The slitter of claim 1 wherein the shroud comprises:
 at least one flange forming the groove,
 wherein the depth of the first groove portion from the axis is less than the depth of the second groove portion from the axis.

10. The slitter of claim 9 wherein the flange flexes to form a snug fit around the elongated body when the guide catheter is advanced over the slitter.

11. The slitter of claim 9 wherein the flange has a thickness of less than 0.015 inches.

12. The slitter of claim 9 wherein the groove has a maximum depth and a width, the maximum depth being greater than the width.

13. The slitter of claim 9 wherein the groove comprises a sloped portion and the retaining finger comprises a sloped edge configured to interact with the groove sloped portion to retain the elongated body therebetween.

14. The slitter of claim 13 wherein the handle includes a horizontal lower edge and each of the groove sloped portion and the retaining finger sloped edge slope at an angle between about 10 degrees and 110 degrees relative to the horizontal lower edge.

15. The slitter of claim 1 wherein the retaining finger comprises a tip having a length, the tip being axially aligned with the shroud when the retaining finger is in a closed position for supporting the elongated body within the shroud.

16. The slitter of claim 1 wherein the nose piece is adapted for insertion into the guide catheter between an outer surface of the elongated body and an inner surface of the guide catheter, the nose piece having a triangular cross-section.

17. The slitter of claim 16 wherein the nose piece extends forward from the slitting blade a distance of up to approximately 0.035 inches.

18. The slitter of claim 16 wherein the nose piece has a maximum width of up to approximately 0.035 inches.

19. The slitter of claim 1 wherein the shroud has a length of at least about one inch for engaging the guide catheter as it is slit.

20. The slitter of claim 1 further comprising a guide rail for engaging a cut wall of the guide catheter.

21. The slitter of claim 1 wherein the handle comprises:
first and second major sides,
a forward edge and a back edge separating the first and second major sides, the back edge comprising a sloped portion and an arcuate portion,
an arcuate top edge extending between the forward edge and the back edge sloped portion, and
a horizontal lower edge extending between the forward edge and the back edge arcuate portion.

22. The slitter of claim 21 further comprising a depression along at least one of the first and second major sides for indicating to a user an intended grip.

23. The slitter of claim 21 wherein at least one of the forward edge and the back edge has a thickness of at least about 0.3 inches.

24. The slitter of claim 21 wherein the first and second major sides have a greatest width of at least approximately 1.7 inches.

25. The slitter of claim 21 wherein the back edge sloped portion has a length of at least one inch.

26. The slitter of claim 21 wherein the handle comprises first and second portions assembled to form a cavity therebetween.

27. The slitter of claim 21 wherein the cavity is configured to receive the holding mechanism.

28. The slitter of claim 21 further comprising a visual alignment feature indicating an intended alignment of the slitter relative to the guide catheter.

29. The slitter of claim 28 wherein the visual alignment feature comprises one of a color contrast between the blade assembly and the handle lower edge and a horizontally extending actuator.

30. The slitter of claim 21 wherein the horizontal lower edge and the forward edge form an approximately ninety degree angle.

31. The slitter of claim 1 wherein the slitting blade comprises means for enhancing the mechanical engagement between the slitting blade and a material used to form the shroud.

32. A slitter for slitting a guide catheter, comprising:
a handle comprising a forward edge;
a blade assembly coupled to the handle comprising a shroud for receiving an elongated body of a medical device and a slitting blade having an exposed cutting edge; and
a holding mechanism coupled to the handle, the holding mechanism comprising:
an actuator; and
a retaining finger coupled to the actuator and axially aligned along the shroud for retaining the elongated body within the shroud, wherein the retaining finger is held in a normally closed position by a bias force provided by a biasing apparatus of the holding mechanism,
at least a portion of the actuator extending forward from the forward edge of the handle and adapted to be depressed into the handle to cause the retaining finger to be laterally displaced in an axial direction from the normally closed position over the shroud corresponding to retaining the elongated body within the shroud to an open position corresponding to releasing the elongated body from the shroud.

33. The slitter of claim 32 wherein the holding mechanism further comprises a lateral arm coupling the actuator to the retaining finger, the lateral arm being axially offset from the retaining finger.

34. The slitter of claim 32 wherein the retaining finger comprising a sloped edge and the shroud comprises a sloped groove for interacting with the retaining finger sloped edge to retain the elongated body within the shroud.

35. A slitter for slitting a guide catheter, comprising:
a handle;
a blade assembly coupled to the handle comprising a shroud for receiving an elongated body of a medical device and a slitting blade having an exposed cutting edge;
retaining means for retaining the elongated body within the shroud, wherein the retaining means is held in a normally closed position by a bias force provided by a biasing apparatus of the slitter; and
displacing means for displacing the retaining means between the normally closed position corresponding to retaining the elongated body within the shroud and an open position corresponding to releasing the elongated body from the shroud.

36. The slitter of claim 35 wherein the displacing means is spring-loaded to cause the retaining means to return to the normally closed position upon release of the displacing means after being depressed to displace the retaining means to the open position.

37. The slitter of claim 35 wherein the displacing means is configured to cause lateral displacement of the retaining means.

38. The slitter of claim 35 wherein the displacing means is configured to cause rotational displacement of the retaining means.

39. The slitter of claim 35 further comprising means for indicating an intended alignment of the slitter relative to the guide catheter.

40. The slitter of claim 35 wherein the handle is configured to accommodate a whole hand grip.

41. A handle for a guide catheter slitter, wherein the guide catheter slitter comprises a slitting blade, the handle comprising:
first and second major sides,
a forward edge and a back edge separating the first and second major sides, wherein the handle is configured such that the slitting blade is located towards the forward edge of guide catheter slitter when assembled with the handle, the back edge comprising a sloped portion and an arcuate portion,
an arcuate top edge extending between the forward edge and the back edge sloped portion, wherein the sloped portion is sloped downward from the arcuate top edge and towards the forward edge, and
a horizontal lower edge extending between the forward edge and the back edge arcuate portion, wherein the arcuate portion is a concave arcuate portion located between the horizontal lower edge and the sloped portion of the back edge,
and further wherein the first and second major sides, forward edge, back edge, arcuate top edge, and horizontal lower edge are configured to accommodate a whole hand grip.

42. The handle of claim 41 further comprising a depression along at least one of the first and second major sides for indicating to a user an intended grip.

43. The handle of claim 41 wherein at least one of the forward edge and the back edge has a thickness of at least about 0.3 inches.

44. The handle of claim 41 wherein the first and second major sides have a greatest width of at least approximately 1.7 inches.

45. The handle of claim 41 wherein the back edge sloped portion has a length of at least one inch.

46. The handle of claim 41 wherein the handle comprises first and second portions assembled to form a cavity therebetween.

47. The handle of claim 46 wherein the cavity is configured to receive a holding mechanism.

48. The handle of claim 41 further comprising a visual alignment feature indicating an intended alignment of the slitter relative to the guide catheter.

49. The handle of claim 48 wherein the visual alignment feature comprises one of a color contrast between the blade assembly and the handle lower edge and a horizontally extending actuator.

50. The slitter of claim 41 wherein the horizontal lower edge and the forward edge form an approximately ninety degree angle.

* * * * *